United States Patent [19]
Milo

[11] 3,938,197
[45] Feb. 17, 1976

[54] CENTRAL FLOW PROSTHETIC CARDIAC VALVE

[76] Inventor: Simcha Milo, 4/19 Edmond Fleg St., Haifa, Israel

[22] Filed: Sept. 3, 1974

[21] Appl. No.: 502,306

[52] U.S. Cl. .................................................. 3/1.5
[51] Int. Cl.² ........................................ A61F 1/22
[58] Field of Search .............................. 3/1, 1.5

[56] References Cited
UNITED STATES PATENTS

| | | |
|---|---|---|
| 3,370,305 | 2/1968 | Goott et al. ............................. 3/1.5 |
| 3,445,863 | 5/1969 | Wada ...................................... 3/1.5 |
| 3,689,942 | 9/1972 | Rapp ....................................... 3/1.5 |
| 3,737,919 | 6/1973 | Child ....................................... 3/1.5 |

Primary Examiner—Ronald L. Frinks
Attorney, Agent, or Firm—Pravel & Wilson

[57] ABSTRACT

A central flow prosthetic cardiac valve for disposition in the heart and the aorta for controlling the pulsatile flow of blood into and from the heart, having a plurality of valve flaps for positive opening and closing of the valve during pulsatile flow of the blood.

13 Claims, 7 Drawing Figures

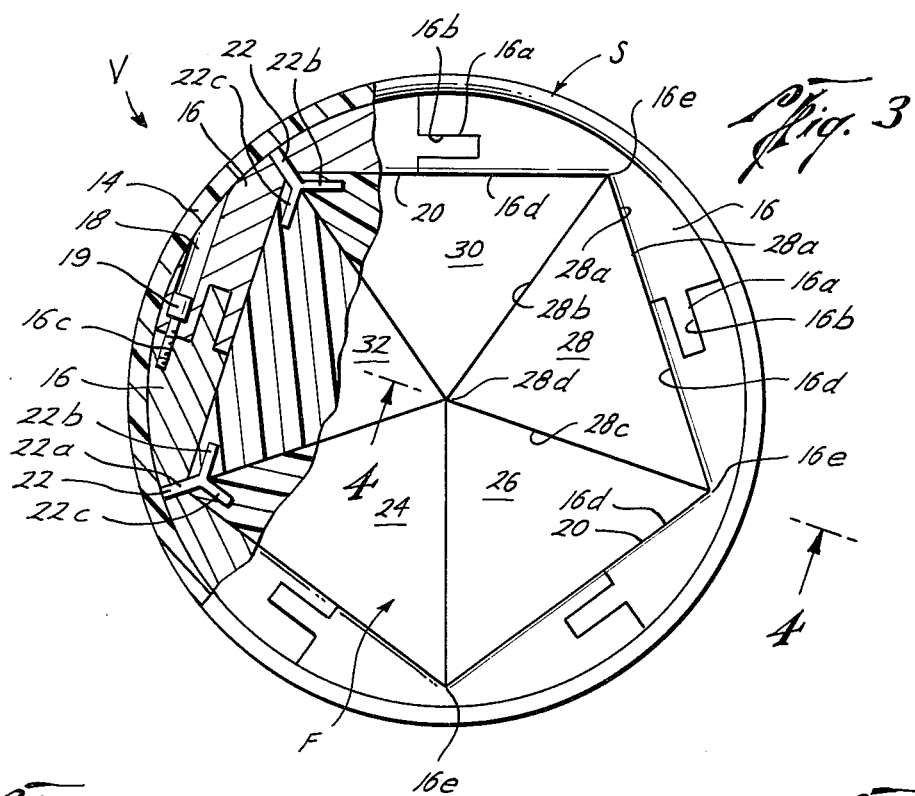
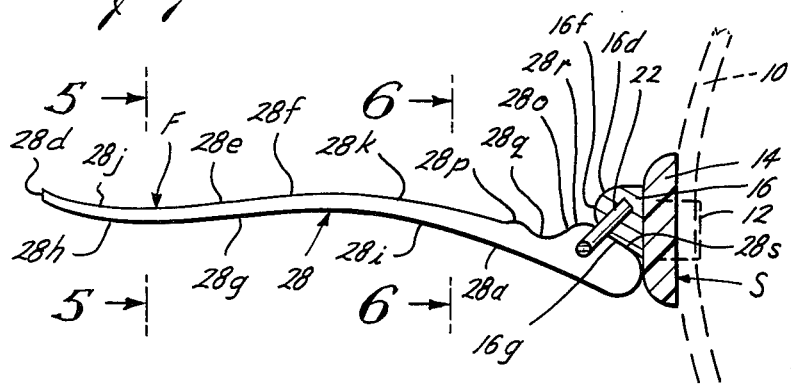
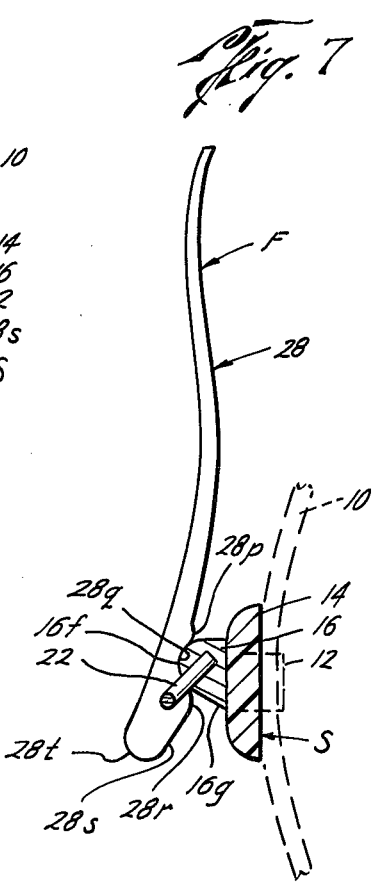
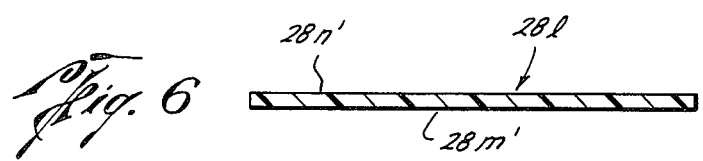

CENTRAL FLOW PROSTHETIC CARDIAC VALVE

BACKGROUND OF THE INVENTION

The field of this invention is prosthetic cardiac valves.

Various types of prosthetic cardiac valves have been developed in recent years, most of which are believed to be described in "The Journal of Cardiovascular Surgery," Volume 63, No. 1, January, 1972, pages 131–142 and in "Journal of the Association for the Advancement of Medical Instrumentation," Volume 5, No. 4, July–August 1971, pages 210–217.

SUMMARY OF THE INVENTION

The present invention relates to a new and improved prosthetic cardiac valve having a plurality of pivotally mounted valve flaps for positive opening and closing thereof during pulsatile flow of blood.

BRIEF DESCRIPTION OF THE DRAWINGS

FIG. 3 is a plan view, partly in section, of the valve of the present invention in a closed position;

FIG. 4 is a sectional view of the present invention, showing the valve flap in a closed position, taken along the lines 4—4 of FIG. 3;

FIG. 5 is a sectional view of the valve flap taken along the lines 5—5 of FIG. 4;

FIG. 6 is the sectional view of the valve flap taken along the lines 6—6 of FIg. 4; and, FIG. 7 is a sectional view similar to FIG. 4, but showing the valve flap of the present invention in an open position.

DESCRIPTION OF THE PREFERRED EMBODIMENT

Figure 1:
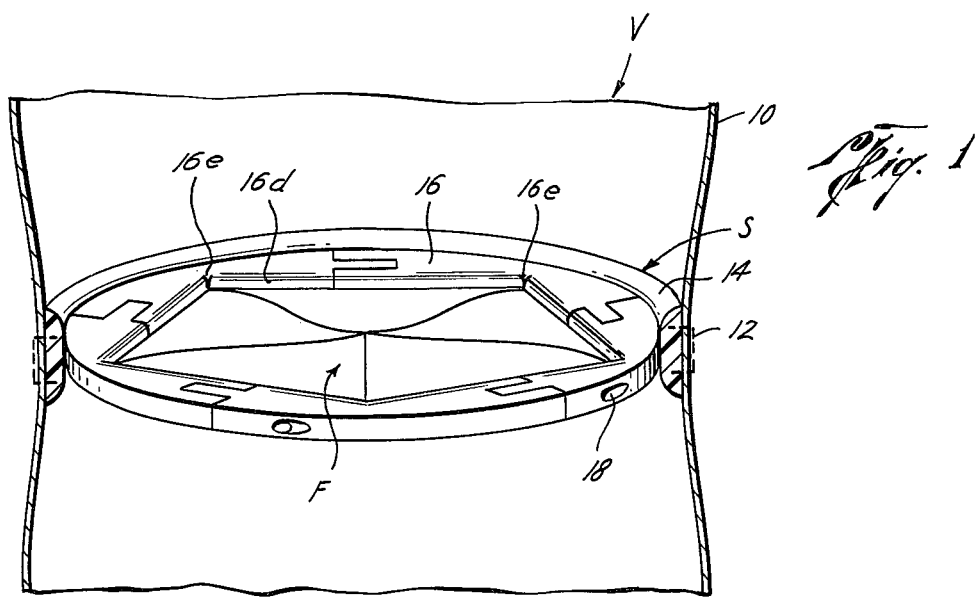
FIG. 1 is an isometric view of the cardiac valve of this invention, shown in the closed position in the aorta.

In the drawings, the letter V designates generally the cardiac valve of this invention which is adapted to be disposed in the heart or in the aorta 10, for replacing the mitral valve, tricuspid valve, or aortic valve, respectively, as will be more evident hereinafter. The valve V is surgically mounted in the aorta 10 by sutures 12, or by any other surgical means as is well known in the art. The cardiac valve V includes an annular valve support S and a plurality of valve flaps F which are adapted to move from a closed position (FIG. 1) to an open positon (FIG. 2) for movements in response to the pulsatile flow of blood from the heart so that the cardiac valve V performs the function of the natural cardiac valve which is replaced by the cardiac valve V.

Considering the invention in more detail, the cardiac valve V includes an annular valve support S having an exterior portion 14 to preferably provide a ring of attaching material such as terephthalate polyester sold under the trademark "DACRON" for securing the annular valve support S to the aorta 10. The surgeon sutures the exterior portion 14 to one of the aortic, mitral, or tricuspid rings with sutures 12, or other suitable surgical means.

The annular valve support S further includes an interior portion made up of a plurality of segments 16 preferably formed of stainless steel or other suitable noncorrosive materials. Each segment 16 includes a male guide 16a (FIG. 3) and a corresponding female guide 16b for positioning interengaging segments adjacent to one another. An opening 18 is formed substantially parallel and adjacent to the female guide 16b for bolt 19 to threadedly engage an adjacent threaded portion 16c formed in segment 16 adjacent to the male guide 16a.

Each segment 16 has a central portion 16d forming an opening 20 in the cardiac valve V. The opening 20 may be of any polygonal configuration, but as illustrated, is in a pentagonal configuration having adjacent central portions 16d adjoining one another about the perimeter of the pentagonal opening 20, having corners 16e formed substantially central thereof each segment 16. As best shown in FIG. 3, flap mounts 22 are formed with the segments 16 at the corners 16e. Each of the flap mounts 22 is preferably of a general "Y" configuration having a portion 22a formed with the segment 16 at the corner 16e and two outwardly extending portions 22b, 22c which will be more fully discussed hereinbelow.

Valve flaps F are disposed about the opening 20 in the annular valve support S. Preferably, the valve flaps F are made of a condensed carbon marketed under the trademark of "PYROLITE". As distinguished from the tear drop-shaped valves of the prior art, the cardiac valve V of the present invention is generally of a flat configuration. As best seen in FIG. 3, the valve flaps F include flap bodies 24, 26, 28, 30, and 32 as equally disposed within the circumference of the annular valve support S about the perimeter of the opening 20. In the preferred embodiment, all valve flaps F are preferably substantially identical to one another. For the purposes of explanation, the hereinbelow disclosure is directed to valve flap body 28, while it is appreciated that the disclosure also applies to all flap bodies 24, 26, 30, 32.

Each of the valve flaps F is preferably of a generally triangular configuration. Flap body 28 (FIG. 3) has a triangular configuration having a base 28a and sides 28b, 28c forming the legs of the triangle, extending inwardly from the base 28a and narrowing to a pointed, narrow end 28d at the intersection of legs 28b, 28c, with the pointed, narrow end 28d being centrally disposed in the opening 20 of the annular valve support S.

As best shown in FIGS. 4 through 7, the valve flap F, while of a generally flat configuration as compared to prior art tear dropped-shaped valves, has a contoured surface as discussed hereinbelow. FIG. 4 shows the contour of flap body 28 from an elevational perspective. A longitudinal curved surface 28e parallels generally the height of the triangular configuration as viewed from the base 28a. The longitudinal curved surface 28e includes substantially parallel upper and lower curved surfaces 28f, 28g respectively wherein lower surface 28g has a substantially convex portion 28h adjacent the narrow end 28d and continuously formed into a substantially concave portion 28i adjacent the base portion 28a. In similar fashion, upper surface 28f has a concave portion 28j substantially paralleling the contour of portion 28h, the concave portion 28j continuously formed into a substantially convex portion 28k which substantially parallels the contour of concave portion 28i.

As best shown in FIG. 5, the valve flap F has a transverse cross sectional portion 28l as looking from the pointed, narrow end 28d towards the base 28a of the flap body 28. The transverse cross sectional portion 28l has a convex surface 28m and an opposing concave surface 28n adjacent to the pointed, narrow end 28d, the surfaces 28m, 28n gradually diminishing in curvature from the narrow, pointed end 28d to substantially flat surfaces 28m', 28n' (FIG. 6) adjacent to the base 28a of the valve body 28 (FIG. 6).

The valve flap F is adapted to be pivotally mounted to the annular valve support S. As best shown in FIGS. 4 and 7, the valve body 28 is pivotally mounted to the annular valve support S by the flap mounts 22 mounted with segments 16. The valve body 28 has appropriately drilled openings (not numbered) such that outwardly extending portions 22b, 22c of the flap mounts 22 may be approriately inserted therein, allowing proper pivotal action therebetween. It should be noted that no single flap mount 22 mounts any one individual flap body 24, 26, 28, 30, 32 for pivotal movement thereof, but that an outwardly extending portion 22b of one flap mount 22 is used in conjunction with the outwardly extending portion 22c of another flap mount 22 such that each valve flap F is mounted by portions of two flap mounts 22. The flap mounts 22 mounted in segments 16 extend downwardly to support the valve flaps F below the segments 16 (FIG. 4, 7).

As noted above, the hinged portion of the valve flap F is formed adjacent to the base 28a of flap body 28 and is pivotally mounted to the annular valve support S by the flap mounts 22 mounted in segments 16. Segments 16 have central portion 16d which serves as a limiting means to limit the extent of opening of the valve flaps F during positive pressure flow of the blood while furthermore restricting the extent of closure of the flaps F during negative pressure flow of the blood. A curved sealing surface 28o is formed adjacent to the hinged portion of the valve flap F for sealably joining the valve flap F to the limiting means formed with central portion 16d of segment 16 to allow pivotal movement of the valve flaps F with respect to the limiting means while remaining in sealable engagement therebetween. More particularly, the limiting means includes surfaces 16f, 16g (FIG. 4, 7) formed with central portion 16d and to be used in conjunction with sealing surface 28o having portions 28p, 28q, 28r, 28s. As shown in FIG. 4, flap surface 28s of the valve flap F is in sealable, flat engagement with surface 16g of the limiting means. Surface 28s is formed adjacent rounded corner 28r adjoining indented portion 28q having a stop portion 28p such that the valve flap F may rotate from a closed position of FIG. 4 to an open position wherein (FIG. 7) the valve flap F remains sealably engaged with the limiting means 16f, 16g as the flap rotates to and from a open and closed position. As shown in FIG. 7, when the valve flap F is in an open position, portion 16f of the limiting means engages the indented portion 28q of the sealing surface 28o, with surfaces 16f and 28q being similarly formed to properly engage one another when the valve is in an open position.

In the assembly of the cardiac valve V of the present invention, the valve flaps F are appropriately positioned on the flap mounts 22 while the segments 16 are loosely held in an interengaging position. Thereafter bolts 19 threadly affix the segments 16 into a unitary structural unit wherein the valve flaps F are pivotally mounted therewith. Exterior portion 14 is thereafter bonded or suitably affixed in any other manner to the assembled segments 16.

Figure 2:
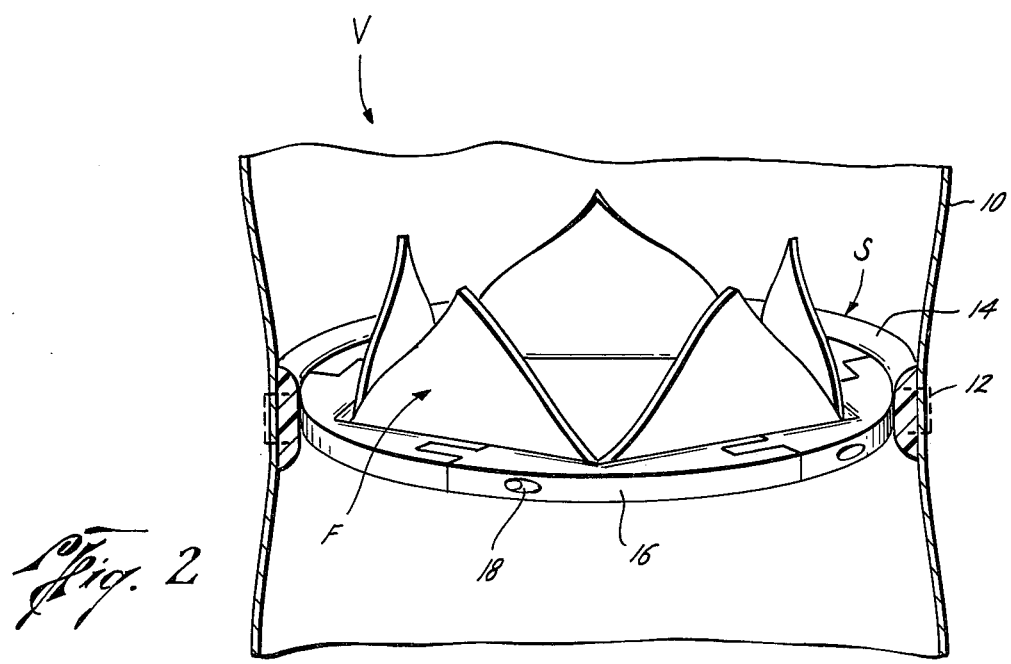
FIG. 2 is a view similar to FIG. 1, but showing the valve in the open position.

In the use or operation of the cardiac valve V of the present invention, the annular valve support S is affixed to the aorta, mitral, or tricuspid rings by sutures 12 affixing the exterior portion 14 to the aorta 10. In response to positive pulsatile flow of blood through the aorta 10, the cardiac valve V as shown in the closed position in FIG. 1, pivotally opens to that position pictured in FIG. 2. Conversely, in response to reverse pulsatile pressure of flow of blood, the cardiac valve V assumes a closed position as shown in FIG. 1. The particular contoured shape of the valve flap F as described hereinabove helps promote proper opening and closing of the cardiac valve V of the present invention. Furthermore, rounded surface 28t (FIG. 7) helps prevent turbulence in the blood flow during positive pulsatile pressure thereof.

Alternatively, instead of having the valve V formed with substantially identical flaps F, they may have modified different configurations. A single flap F or any number of flaps F hinged for opening and closing in accordance with the teachings of this invention could be provided.

The foregoing disclosure and description of the invention are illustrative and explanatory thereof, and various changes in the size, shape, and materials as well as in the details of the illustrated construction may be made without departing from the spirit of the invention.

I claim:

1. A prosthetic cardiac valve adapted to be disposed in the aortic, mitral, or tricuspid rings, comprising:
    an annular valve support having an exterior portion adapted to be attached to the aortic, mitral, or tricuspid rings and an interior portion forming an opening;
    a plurality of adjacent valve flaps, each of said flaps being pivotally mounted to said annular valve support in circumferential disposition about said interior portion of said valve support to close said opening by engagement between said adjacent valve flaps and said valve support, wherein said valve flaps move from a closed position to an open position during positive pulsatile flow of blood through said opening in said interior portion of said valve support;
    each of said valve flaps has a contoured surface area of a substantially triangular configuration with a hinged portion at the base of said substantially triangular configuration and a narrow end at the apex of said substantially triangular configuration, said hinged portion being pivotally mounted with said interior portion of said valve support and said narrow end extending into said opening formed in said valve support such that said valve flaps adjacent to one another effectively close said opening when said flaps are in said closed position; and,
    each of said flaps includes a curved sealing surface formed adjacent said hinged portion of said flap cooperating with means on said valve support for sealably joining said flap to said valve support to allow pivotal movement of said flap with respect to said valve support while remaining in sealable engagement therebetween in the open or closed position.

2. The structure of claim 1, wherein said contoured surface of each of said flaps includes:
    a transverse cross-sectional portion transverse to the height and parallel to the base of said substantially triangular configuration at said narrow end of said flap having a substantially convex surface facing positive pulsatile pressure flow of blood and an opposing substantially concave surface facing the reverse pulsatile pressure of flow of blood to cause said flap to open under positive pressure of blood and to close under negative pressure of blood, said convex surface and said concave surface gradually diminishing in curvature from said narrow end to a substantially flat surface at said hinged portion of said flap for proper pivotal action thereof.

3. The structure of claim 1, wherein said contoured surface of each of said flaps further includes:
a longitudinal curved surface paralleling the height of said generally triangular configuration, said longitudinal curved surface facing the positive pulsatile flow of blood having a substantially convex configuration adjacent said narrow end and continuously formed into substantially concave configuration adjacent said hinged portion for positive opening of said flaps during such pulsatile flow.

4. The structure of claim 1, wherein each of said flaps further includes:
limiting means integrally formed with said interior portion of said valve support adjacent said curved sealing surface adjacent said hinged portion of each of said flaps to limit the extent of opening of said flaps during positive pressure flow of blood and to restrict the extent of closure of said flaps during negative pressure flow of blood.

5. The structure of claim 4, further including:
pivotal mounting means integrally formed with said limiting means for pivotally mounting said hinged portion of each of said flaps to said interior portion of said valve support.

6. The structure of claim 5, wherein:
each of said flaps is pivotally mounted adjacent to and below said limiting means by said pivotal mounting means.

7. The structure of claim 6, wherein said pivotal mounting means includes:
a plurality of unitary flap mounts, each of said mounts capable of pivotally mounting one end of the base of each of said triangularly shaped flaps adjacent to one another, each of said mounts being generally of a "Y" configuration.

8. The structure of claim 1, wherein said annular valve support includes:
a plurality of individual circumferential interengaging segments, each of said segments being mounted adjacent to one another, said segments providing for said pivotal mounting of said flaps with said valve support.

9. The structure of claim 1, wherein:
said valve flaps are disposed substantially equally about the circumference of said opening of said valve support in substantially a pentagonal configuration.

10. In a prosthetic cardiac valve adapted to be disposed within the aortic, mitral, or tricuspid rings, having an annular valve support forming an opening and at least one valve flap pivotally disposed about the annular valve support to close said opening, the improvement residing in the valve flap which comprises:
a generally flat body of a generally triangular configuration having a base pivotally mounted on the valve support at a hinged portion thereof and an end opposite said base and adapted to close the opening in the annular valve support when in the closed position and to pivot to open the same; and,
a curved sealing surface formed adjacent said hinged portion of said flap body cooperating with means on said valve support for sealably joining said flap body with the valve support while the valve is in an open or a closed position.

11. The valve flap of claim 10, further including:
pivot means at each end of said base for pivotally mounting said flap body to the annular valve support.

12. The valve flap of claim 10, wherein said generally flat flap body includes a contoured surface having:
a transverse cross-sectional portion transverse to the height and parallel to the base of said substantially triangular configuration at said narrow end of said flap having a substantially convex surface facing positive pulsatile pressure flow of blood and an opposing substantially concave surface facing the reverse pulsatile pressure of flow of blood to cause said flap to open under positive pressure of blood and to close under negative pressure of blood, said convex surface and said concave surface gradually diminishing in curvature from said narrow end to a substantially flat surface at said hinged portion of said flap for proper pivotal action thereof.

13. The valve flap of claim 10, further including:
a longitudinal curved surface paralleling the height of said generally triangular configuration, said longitudinal curved surface facing the positive pulsatile flow of blood having a substantially convex configuration adjacent said narrow end and continuously formed into substantially concave configuration adjacent said hinged portion for positive opening of said flaps during such pulsatile flow.

* * * * *